United States Patent
Clarke

(10) Patent No.: US 8,448,785 B2
(45) Date of Patent: *May 28, 2013

(54) SYRINGE DISPOSAL DEVICE

(75) Inventor: Nicholas Edward Clarke, Penrith (AU)

(73) Assignee: ASP Rights Management Pty Limited (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/836,042

(22) Filed: Jul. 14, 2010

(65) Prior Publication Data

US 2010/0276319 A1 Nov. 4, 2010

Related U.S. Application Data

(63) Continuation of application No. 12/102,114, filed on Apr. 14, 2008, now Pat. No. 7,775,357.

(51) Int. Cl.
*B65D 83/10* (2006.01)

(52) U.S. Cl.
USPC .......................................... 206/365

(58) Field of Classification Search
USPC .......... 206/365, 363, 306, 366, 364; 604/192, 604/263, 187
See application file for complete search history.

(56) References Cited

U.S. PATENT DOCUMENTS

| | | | | |
|---|---|---|---|---|
| 1,378,806 A | * | 5/1921 | Ausubel | 206/210 |
| 3,342,319 A | * | 9/1967 | Faulseit | 206/365 |
| 3,712,302 A | | 1/1973 | Burke et al. | |
| 4,332,323 A | | 6/1982 | Reenstierna | |
| 4,634,428 A | | 1/1987 | Cuu | |
| 4,728,320 A | | 3/1988 | Chen | |
| 4,964,866 A | * | 10/1990 | Szwarc | 604/192 |
| 5,147,325 A | | 9/1992 | Mitchell et al. | |
| 5,611,429 A | * | 3/1997 | Phillips | 206/365 |
| 5,934,460 A | * | 8/1999 | Schmid | 206/210 |

FOREIGN PATENT DOCUMENTS

| | | |
|---|---|---|
| GB | 2198353 | 6/1988 |
| JP | 09019498 | 1/1997 |
| WO | 0123019 | 4/2001 |

* cited by examiner

*Primary Examiner* — Jacob K Ackun
*Assistant Examiner* — Jenine Pagan
(74) *Attorney, Agent, or Firm* — Design IP

(57) ABSTRACT

The present invention discloses a syringe disposal device (10) for a single syringe (1) having an elongate body (2) with a needle (3) at one end and a finger engageable flange (4) at its other end. The device (10) comprises an elongate enclosed sheath (12) having a closed tip (14) at one end and a cuff (16) at the other end. A syringe detention device (26) is located adjacent the cuff (16) and has at least one inclined sloping surface (28) each of which has a frangible portion (31) rupturable by the syringe flange (4) passing the surface (28) to convert the sloping surface (28) into a cantilevered strip (28A).

6 Claims, 3 Drawing Sheets

Figure 3:
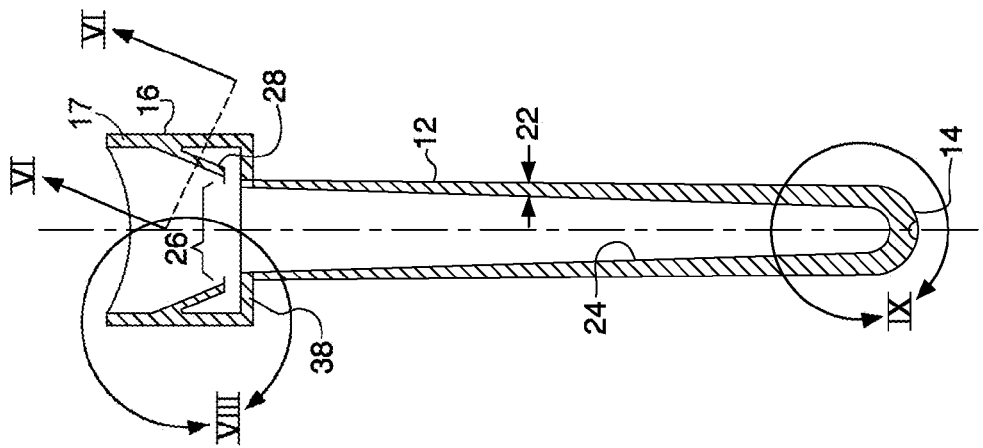

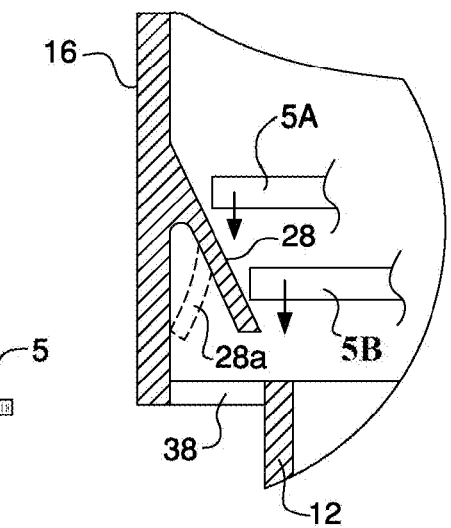
FIG. 8
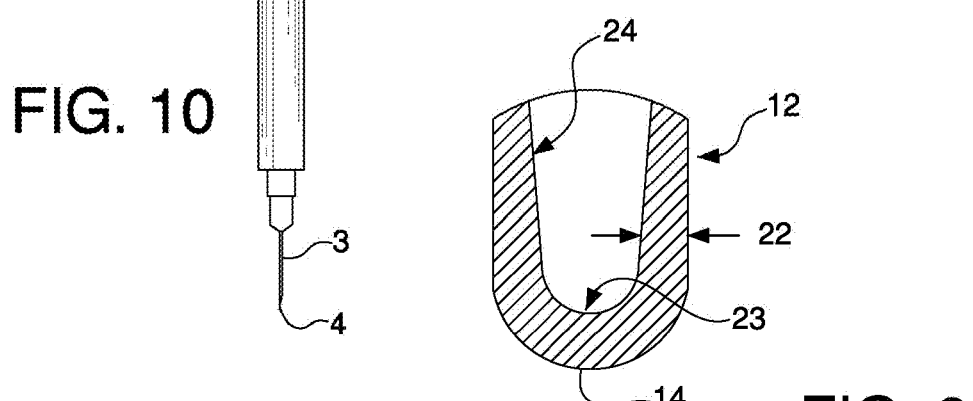
FIG. 10
FIG. 9
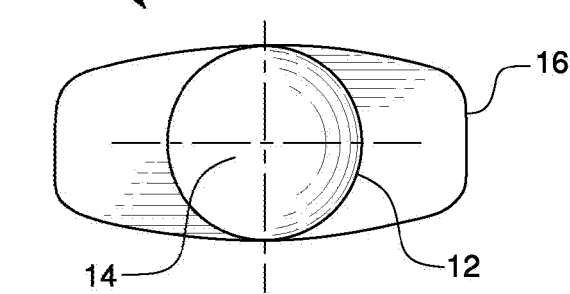
FIG. 11

SYRINGE DISPOSAL DEVICE

CROSS REFERENCE TO RELATED APPLICATIONS

This application is a Continuation application of U.S. patent application Ser. No. 12/102,114, filed Apr. 14, 2008, which is incorporated by reference herein in its entirety.

FIELD OF INVENTION

The present invention relates to syringes and, in particular, to the safe disposal of syringes.

BACKGROUND

It is well known that syringes should be safely disposed of after use in order to prevent needle stick injuries, the spread of disease, and the like. It is known to provide a container to dispose of multiple numbers of syringes and examples of such containers are disclosed in U.S. Pat. No. 5,277,312 (Vumbaca) and Australian Patent No. 741,793 (License Management Pty Ltd).

It is also known to provide a disposal container for an individual syringe and one such container is disclosed in International Application No. WO 01/23019. With reference to the drawings of that published International application, that specification discloses a syringe 38 having a finger engaging flange 38a which has two extremities 38aa. These extremities engage with the inner surfaces 17a of a wall 16 formed around the periphery of the container. Once the flange 38a is pushed past the wall 16 thereby deflecting same slightly, the syringe 38 is retained within the disposal device.

The abovementioned arrangement suffers from a number of disadvantages. The first of these is that the wall 16 is relatively rigid and therefore it can be quite difficult to push the syringe fully home and into the disposal device so as to permanently retain the same within the device. This is particularly the case for the elderly or the infirm. Furthermore, the distance between the flange extremities 38aa and the corresponding walls 16 must be closely matched in order that the necessary degree of deflection takes place. If the flange is too small the syringe will not be retained within the device and if the flange is too bid the syringe cannot be fully pushed into the device. That is to say, the prior art device does not accept a wide range of syringe sizes.

The aim of the present invention is to substantially overcome, or at least ameliorate, the abovementioned difficulties.

SUMMARY

In accordance with a first aspect of the present invention there is disclosed a syringe disposal device for a single syringe having an elongate body with a needle at one end and a finger engageable flange at its other end, said device comprising an elongate enclosed sheath having a closed tip at one end and a syringe body receiving opening at the other end, wherein a syringe retaining means is located adjacent said opening and comprises at least one inclined sloping surface each of which has a frangible portion rupturable by said syringe flange passing said surface to convert each said sloping surface into a cantilevered strip.

In accordance with a second aspect of the present invention there is disclosed a syringe disposal device for a single syringe having an elongate body with a needle at one end and a finger engageable flange at its other end, said device comprising an elongate enclosed sheath having a closed tip at one end and a syringe body receiving opening at the other end, with a syringe retaining means located adjacent said opening, wherein said sheath has a wall thickness which increases from said opening towards said tip.

In accordance with a third aspect of the present invention there is disclosed a method of disposing of an individual syringe, said method comprising the steps of:
(i) inserting the tip of the needle of said syringe into the opening of said device as defined above;
(ii) continuing said insertion until said needle tip engages said sheath closed tip and is permanently deflected thereby; and
(iii) continuing said insertion until said syringe finger engageable flange is engaged with said syringe retaining means.

BRIEF DESCRIPTION OF THE DRAWING(S)

Figure 2:
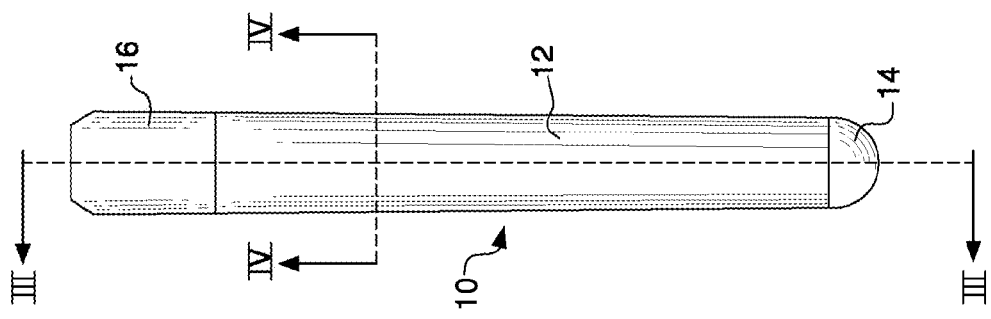
Figure 1:
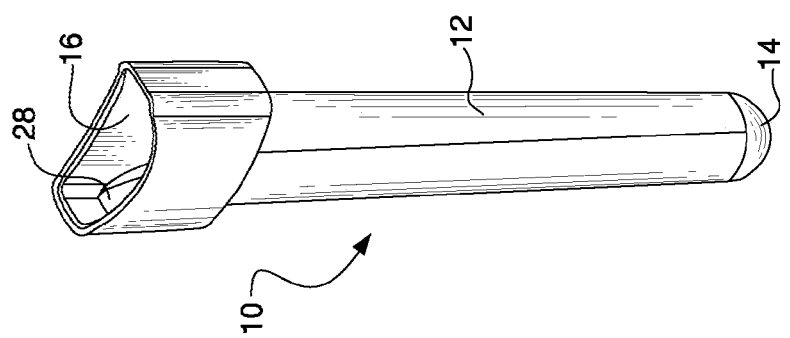
Figure 4:
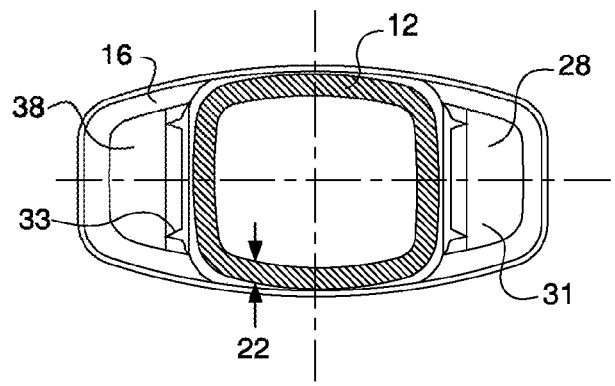
Figure 5:
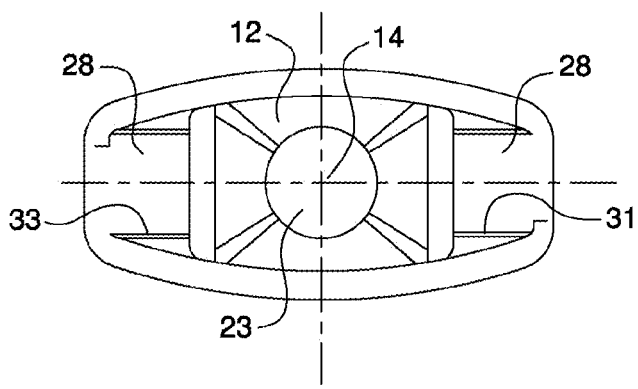
Figure 6:
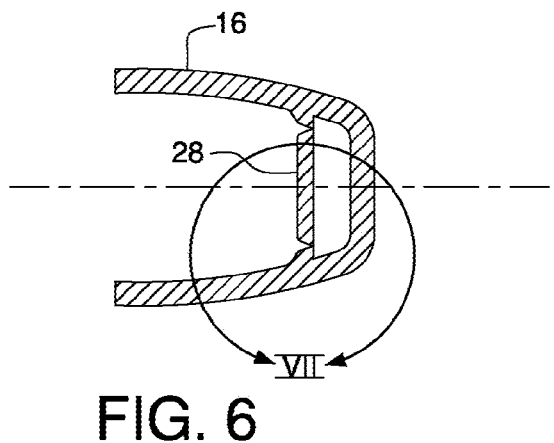
Figure 7:
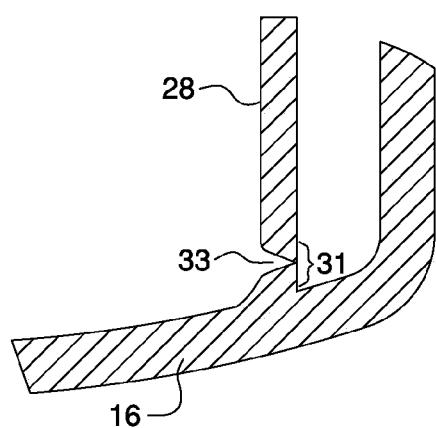

A preferred embodiment of the present invention will now be described with reference to the drawings in which:
FIG. 1 is a perspective view of the disposal device of the preferred embodiment.
FIG. 2 is a side elevation of the device of FIG. 1.
FIG. 3 is a vertical cross sectional view taken along the line III-III of FIG. 2.
FIG. 4 is a transverse cross sectional view taken along the line IV-IV of FIG. 2.
FIG. 5 is plan view of the device of FIG. 1.
FIG. 6 is a cross sectional view taken along the line VI-VI of FIG. 3.
FIG. 7 is an enlarged view of a portion of FIG. 6.
FIG. 8 is an enlarged view of a portion of FIG. 3.
FIG. 9 is an enlarged view of the tip of the device illustrated in FIG. 3.
FIG. 10 is side elevation of a conventional syringe.
FIG. 11 is a bottom view of the device of FIG. 1.

DETAILED DESCRIPTION OF THE PREFERRED EMBODIMENT(S)

With reference to FIG. 10 a conventional syringe 1 has an elongate body 2 with a needle 3 at its leading end. The needle 3 has a tip 4. At the other end of the body 2 is a finger engaging flange 5. The syringe 1 also has a moveable plunger 6.

With the foregoing in mind, the disposal device 10 of the preferred embodiment takes the form of a sheath 12 having a tip 14 at one end and a cuff 16 formed from a peripheral wall 17, at the other end.

As best seen in FIG. 3, the sheath 12 has an increasing wall thickness 22 which progressively increases traveling from the cuff 16 towards the tip 14. As best seen in FIG. 9, the wall thickness of the sheath 12 is at a maximum at the tip 14 and the interior of the tip is formed into a substantially hemispherical dome 23. In addition, the interior surface 24 of the sheath 12 is smooth and is not provided with any steps or snags.

Located within the cuff 16 is a syringe detention device 26 which as best seen in FIGS. 3, 4, 5 and 8 takes the form of two mutually inclined sloping surfaces 28 which each extend from one side of the cuff 16 to the other. As best appreciated from FIGS. 6 and 7, each of the sloping surfaces 28 has two frangible portions 31 which preferably each take the form of a V-shaped groove which very nearly, but not quite, extends through the entire thickness of the sloping surfaces 28.

As best appreciated from FIGS. 3 and 8, aligned with each of the sloping surfaces 28 is an aperture 38 between the cuff 16 and the sheath 12. As the disposal device 10 is preferably moulded from plastics material, the two apertures 38 are preferably formed by means of a mould pin (not illustrated) which occupies the space between the apertures 38 and the sloping surfaces 28 during the moulding procedure and which are extracted via the apertures 38 once the disposal device 10 has been moulded. As best seen in FIG. 8, the sloping surfaces 28 extend away from the wall 16 by a distance equivalent to the size of the aperture 38.

As seen in FIG. 8, if a syringe 1 has a relatively small flange such as flange 5B, when the syringe 1 is inserted into the device 10 the extremities of the flange 5B merely cause a deflection of the sloping surfaces 28 as the syringe 1 is pushed into the device 10. Once the flange 5B has passed beyond the inner edge of the sloping surfaces 28, then the syringe is retained in the retention device formed by the cuff 16 and sloping surfaces 28.

However, if the syringe 1 should be of a larger size and have a flange such as flange 5A indicated in FIG. 8, then as the flange 5A comes into contact with the sloping surface 28, the grooves 33 are broken. Thus each sloping surface 28 is converted into a cantilevered strip which bends as indicated by dashed lines in FIG. 8 into the curved configuration designated 28A. In the curved configuration 28A the cantilevered strip is easily able to accommodate flange 5A moving therepast but the natural resilience of the plastic ensures that the strip 28A returns to the original position of the sloping surface 28 thus capturing the flange 5A and retaining the syringe 1 within the retention device 10.

It will be appreciated by those skilled in the art that the length of the sheath 12 is such that the tip 14 is spaced from the apertures 38 by a distance less than that of the tip 4 and flange 5 of the syringe 1. As a consequence, as the tip 4 of the needle 3 approaches the tip 14, the needle 3 is bent, usually into a generally U-shaped configuration, which renders the syringe 1 inoperable. In particular, because the thickest part of the wall of the sheath 12 is located at the tip 14, there is no danger of the tip 4 of the needle 3 penetrating through the wall thickness 22 of the sheath 12.

The above described arrangement provides a number of substantial advantages. Firstly, the disposal device 10 maybe easily moulded using conventional moulding techniques such as extraction pins. Secondly, the retention device 26 enables a wide range of syringes to be accepted within the device. Thirdly, the sheath wall thickness 22 increasing from the cuff 16 towards the tip 14 ensures that the needle 3 is safely contained within the sheath 12.

The foregoing describes only one embodiment of the present invention and modifications, obvious to those skilled in the art, can be made thereto without departing from the scope of the present invention.

The term "comprising" (and its grammatical variations) as used herein is used in the inclusive sense of "including" or "having" and not in the exclusive sense of "consisting only of."

What is claimed is:

1. A syringe disposal device for a single syringe, the syringe having an elongate body with a needle at one end and a finger engageable flange at its other end, said device comprising:
   an elongate enclosed sheath having a closed tip at one end and a syringe body receiving opening at the other end; and
   a syringe retaining means located adjacent said syringe body receiving opening;
   wherein said sheath has a wall thickness, said wall thickness increasing from said syringe body receiving opening towards said closed tip.

2. The device as defined in claim 1 wherein the interior of said sheath is smooth and unstepped.

3. The device as defined in claim 2 wherein the interior of said tip of said sheath is substantially hemispherical.

4. A method of disposing of an individual syringe having a needle tip, said method comprising the steps of:
   (i) inserting the needle tip of said syringe into an opening of a syringe disposal device for a single syringe, the syringe also having a finger engageable flange at its other end opposing the needle tip, the syringe disposal device also having an elongate enclosed sheath having a closed tip at the end opposing the opening and a syringe retaining means located adjacent said opening, wherein said elongate enclosed sheath has a wall thickness, said wall thickness increasing from said opening towards said closed tip;
   (ii) continuing said insertion until said needle tip engages said sheath closed tip and is permanently deflected thereby; and
   (iii) continuing said insertion until said finger engageable flange is engaged with said syringe retaining means.

5. The device as defined in claim 1 wherein said wall thickness progressively increases from said syringe body receiving opening towards said closed tip.

6. The device as defined in claim 1 wherein said wall thickness progressively increases from said syringe body receiving opening towards said closed tip.

\* \* \* \* \*